US010528763B2

(12) United States Patent
Popescu

(10) Patent No.: US 10,528,763 B2
(45) Date of Patent: Jan. 7, 2020

(54) METHOD OF PROTECTING DATA EXCHANGED BETWEEN A SERVICE USER AND A SERVICE PROVIDER

(71) Applicant: Siemens Healthcare GmbH, Erlangen (DE)

(72) Inventor: Stefan Popescu, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/318,747

(22) PCT Filed: Jun. 16, 2017

(86) PCT No.: PCT/EP2017/064784
§ 371 (c)(1),
(2) Date: Jan. 18, 2019

(87) PCT Pub. No.: WO2018/015081
PCT Pub. Date: Jan. 25, 2018

(65) Prior Publication Data
US 2019/0286850 A1 Sep. 19, 2019

(30) Foreign Application Priority Data
Jul. 20, 2016 (EP) .................................... 16180367

(51) Int. Cl.
H04L 29/06 (2006.01)
G06F 21/62 (2013.01)
(Continued)

(52) U.S. Cl.
CPC ......... *G06F 21/6254* (2013.01); *G16H 10/60* (2018.01); *G16H 30/40* (2018.01);
(Continued)

(58) Field of Classification Search
CPC ........ G06F 21/60; G06F 21/606; G06F 21/62; G06F 21/6254; G06F 21/6245
See application file for complete search history.

(56) References Cited

U.S. PATENT DOCUMENTS 7,548,915 B2 * 6/2009 Ramer ............... G06Q 30/0243
705/14.54
7,953,762 B2 * 5/2011 Agrawal ............. G06Q 10/067
707/802
(Continued)

FOREIGN PATENT DOCUMENTS

CN 103631175 A 3/2014
CN 105144164 A 12/2015
(Continued)

OTHER PUBLICATIONS

Intention to Grant EPO Form 2004C for European Application No. 16180367.1 dated May 14, 2018.
(Continued)

*Primary Examiner* — Hosuk Song
(74) *Attorney, Agent, or Firm* — Harness, Dickey & Pierce, P.L.C.

(57) ABSTRACT

The invention discloses a method of protecting data exchanged between a service user and a service provider, which method comprises the steps of encoding data by converting meaningful content of the data into meaningless content to obtain encoded upload data for sending to the service provider; processing the encoded upload data at the service provider to obtain encoded download data for sending to the service user; and decoding the encoded download data by converting meaningless content of the encoded download data into meaningful content of download data.

19 Claims, 8 Drawing Sheets

(51) Int. Cl.
  *G16H 10/60* (2018.01)
  *G16H 50/20* (2018.01)
  *G16H 50/70* (2018.01)
  *G16H 30/40* (2018.01)
(52) U.S. Cl.
  CPC ............ *G16H 50/20* (2018.01); *G16H 50/70* (2018.01); *H04L 63/0421* (2013.01)

(56) References Cited

U.S. PATENT DOCUMENTS

| | | | |
|---|---|---|---|
| 8,156,128 B2* | 4/2012 | Ramer | G06Q 30/02 705/14.53 |
| 9,971,317 B2* | 5/2018 | Maturana | G06F 9/5072 |
| 10,148,989 B2* | 12/2018 | Amidei | H04N 21/23439 |
| 2004/0078238 A1 | 4/2004 | Thomas | |
| 2008/0118150 A1 | 5/2008 | Balakrishnan | |
| 2009/0049069 A1 | 2/2009 | Aggarwal et al. | |
| 2012/0177248 A1 | 7/2012 | Shuster | |
| 2013/0139268 A1 | 5/2013 | An | |
| 2014/0058543 A1 | 2/2014 | Gerding et al. | |
| 2014/0279773 A1 | 9/2014 | Chen et al. | |
| 2015/0149208 A1 | 5/2015 | Lynch et al. | |
| 2016/0321468 A1 | 11/2016 | Stankiewicz et al. | |
| 2017/0200256 A1 | 7/2017 | Wiemker et al. | |
| 2019/0258927 A1 | 8/2019 | Chen et al. | |

FOREIGN PATENT DOCUMENTS

| | | |
|---|---|---|
| CN | 105760932 A | 7/2016 |
| WO | WO 2015073260 A1 | 5/2015 |
| WO | WO 2015197541 A1 | 12/2015 |

OTHER PUBLICATIONS

European Search Report EPO Form 1507N for European Application No. 16180367.1 dated Oct. 21, 2018.
European Office Action EPO Form 2001 for European Application No. 16180367.1 dated Dec. 18, 2017.
European Office Action EPO Form 2001 for European Application No. 16180367.1 dated Apr. 24, 2017.
European Office Action EPO Form 2001 for European Application No. 16180367.1 dated Sep. 5, 2017.
International Search Report PCT/ISA/210 for PCT International Application PCT/EP2017/064784 dated Sep. 13, 2017.
Written Opinion PCT/ISA/237 for PCT International Application PCT/EP2017/064784 dated Sep. 13, 2017.
Chinese Office Action and English translation thereof dated Aug. 5, 2019.

* cited by examiner

FIG 3

| Patient name: John Kerry Clinical data | Values | Statistical significance |
|---|---|---|
| Age | 66 | *** |
| Total cholesterol (mg/dL) | 230 | ** |
| Gender (male/female) | male | * |
| Cigarettes/day | 24 | ** |
| HDL cholesterol (mg/dL) | 45 | *** |
| Systolic blood pressure (mm Hg) | 150 | ** |
| Diabetes mellitus (yes/no) | yes | *** |
| Chronic Kidney Disease (yes/no) | no | ** |
| Predicted CVD risik: | 67% | |

METHOD OF PROTECTING DATA EXCHANGED BETWEEN A SERVICE USER AND A SERVICE PROVIDER

PRIORITY STATEMENT

This application is the national phase under 35 U.S.C. § 371 of PCT International Application No. PCT/EP2017/064784 which has an International filing date of Jun. 16, 2017, which designated the United States of America and which claims priority to European Patent Application No. EP 16180367.1 filed Jul. 20, 2016, the entire contents of which are hereby incorporated herein by reference.

FIELD

Embodiments of the invention generally relate to a method of protecting data exchanged between a service user and a service provider, and a data protection system.

BACKGROUND

Processing of large amounts of data may be carried out by a service provider for a service user for various reasons. For example, an owner of large quantities of healthcare data might prefer to pay for cloud storage and computing resources instead of carrying the cost of the storage and processing hardware. The service user can grant the service provider access to data in order to run algorithms that extract additional value out of data, for example to train a statistical model or a deep learning algorithm. A model or algorithm trained in this way will later be able to process working data to extract information, for example to make predictions.

Data privacy provisions require that neither the service provider nor an unauthorized person such as an eavesdropper or cyber-intruder is able to make use of the service user's data, for example with the aim of exposing confidential content. The service user also needs to be certain that no other party will be able to use the data for illicit purpose, for example to run other analytical tools on the data or to use the models trained on the service user's data to generate commercial benefits.

The established way of dealing with sensitive data such as patient records is to anonymize the data before sending it to a service provider with the aim of training and developing new analytics methods such as statistical models, prediction models or computer-assisted diagnostic tools. Often, it is not sufficient to anonymize only the patient name but it is also necessary to hide other data fields that would permit patient identification by an intruder. Such data fields may include patient contact data, age, weight, height, DNA data, medical images, laboratory values, diseases and therapy history. However, this approach creates additional problems: for example, concealing such data makes it unavailable for training and learning algorithms, so that the accuracy of an analytics models will suffer significantly.

While sensitive data can be encrypted before transferring between service user and service provider, an eavesdropper might still conceivably be able to decrypt the intercepted data and access the content. Another weak link in this setup is that the service provider must decrypt the received input data before feeding it to a model or analytics tool. At this stage, the data is vulnerable to theft by an unauthorized person at the service provider end. Furthermore, a model or tool trained on that content may be used by an unauthorized person.

SUMMARY

At least one embodiment of the invention provides a way of exchanging data between a service user and a service provider that improves upon or even overcomes at least one of the problems outlined above. Embodiments of the invention are directed to a method of transferring data between a service user and a service provider; and a data protection system.

According to at least one embodiment of the invention, the method of protecting data exchanged between a service user and a service provider comprises:

encoding upload data by converting relevant content of the upload data into meaningless content;

uploading the encoded upload data to the service provider;

processing the encoded upload data at the service provider to obtain encoded output data;

downloading the encoded output data to the service user; and decoding the encoded output data by converting meaningless content back into relevant content.

According to an embodiment of the invention, the data protection system of a service user comprises an encoder module realized to convert relevant content of upload data into meaningless content prior to uploading from the service user to a service provider;

a data transfer interface realized to upload encoded data to the service provider and to download encoded data from the service provider; and a decoder module realized to convert meaningless content of the download data into relevant content.

Other objects and features of the present invention will become apparent from the following detailed descriptions of the example embodiments considered in conjunction with the accompanying drawings. It is to be understood, however, that the drawings are designed solely for the purposes of illustration and not as a definition of the limits of the invention.

FIG. 3 shows tabular data collected by a service user;

Figure 4:
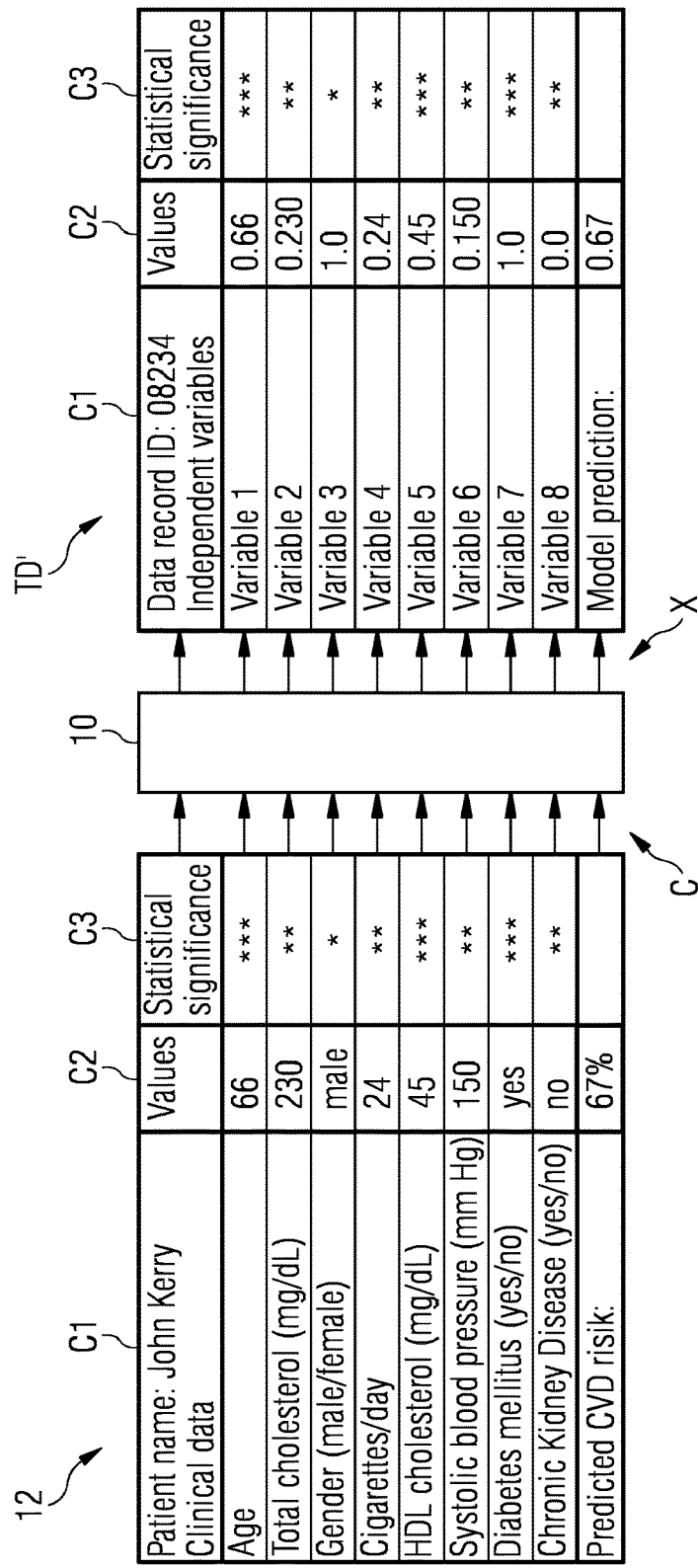
Figures 5, 5A:
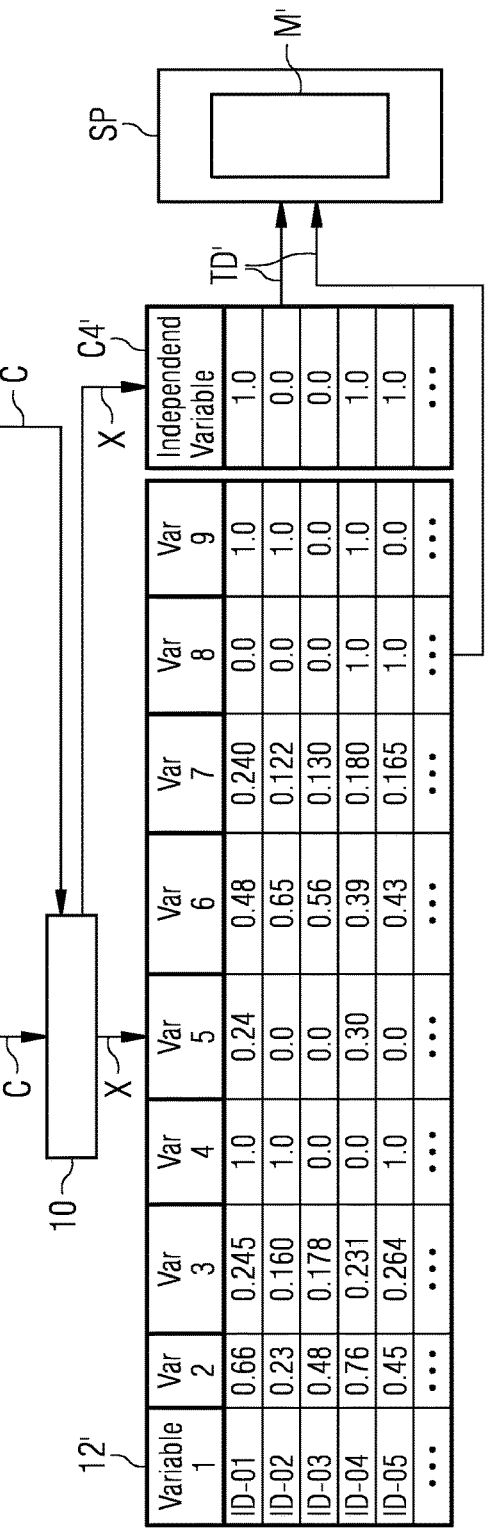
Figure 5B:
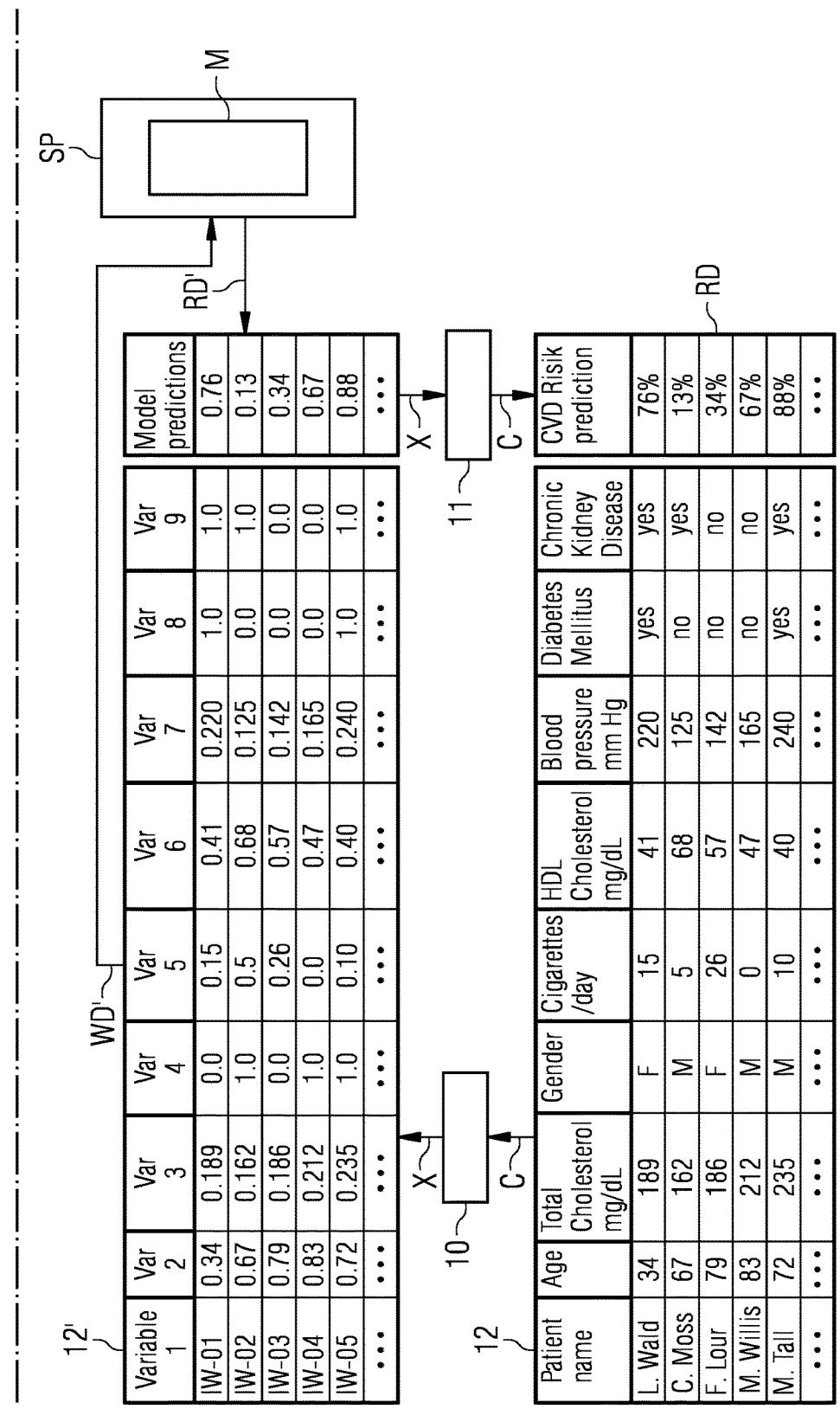
Figure 6:
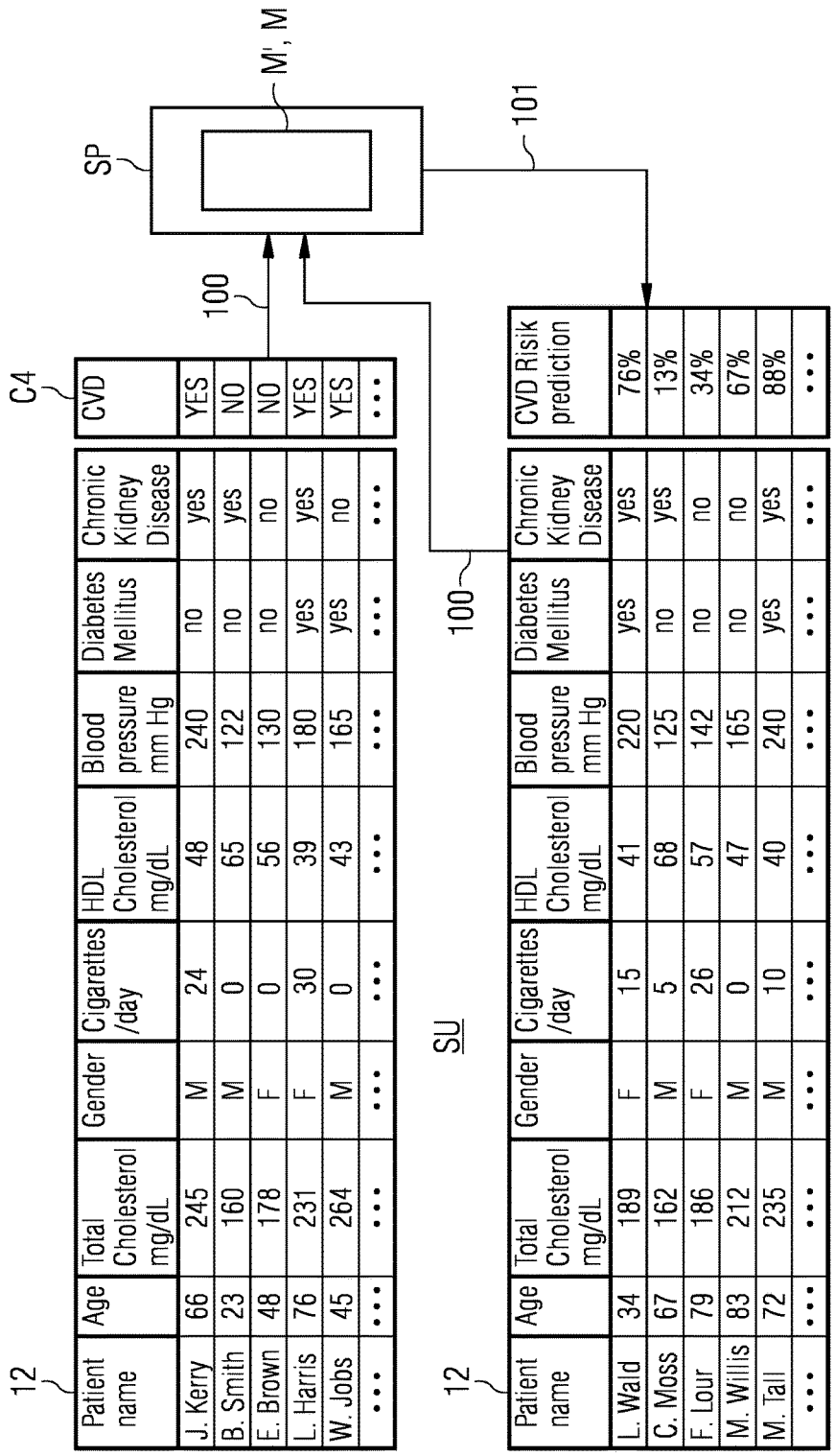
Figure 7:
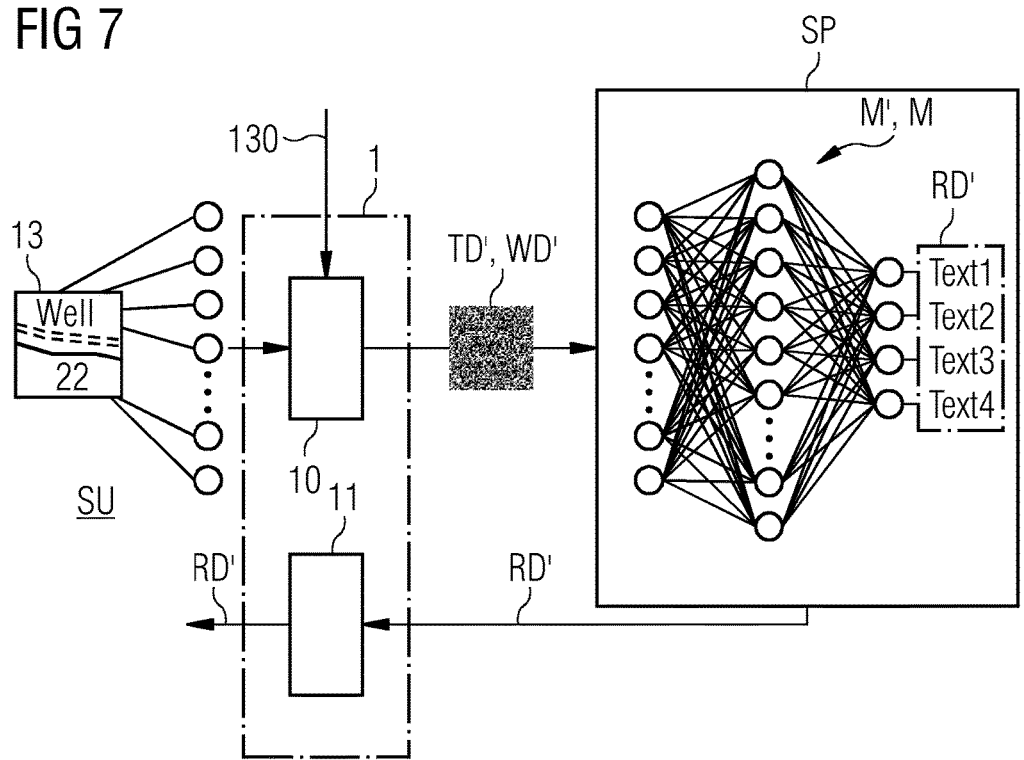
Figure 8:
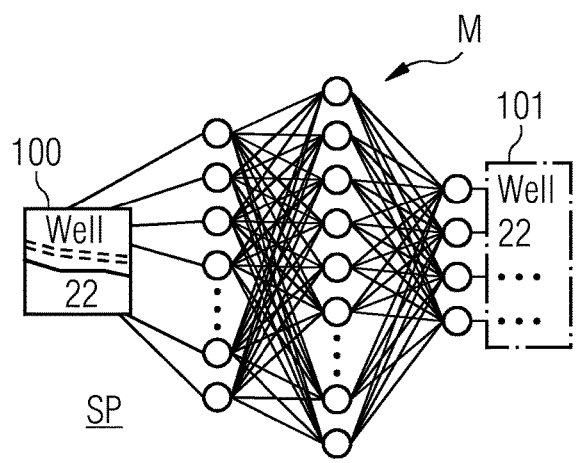
Figure 9:
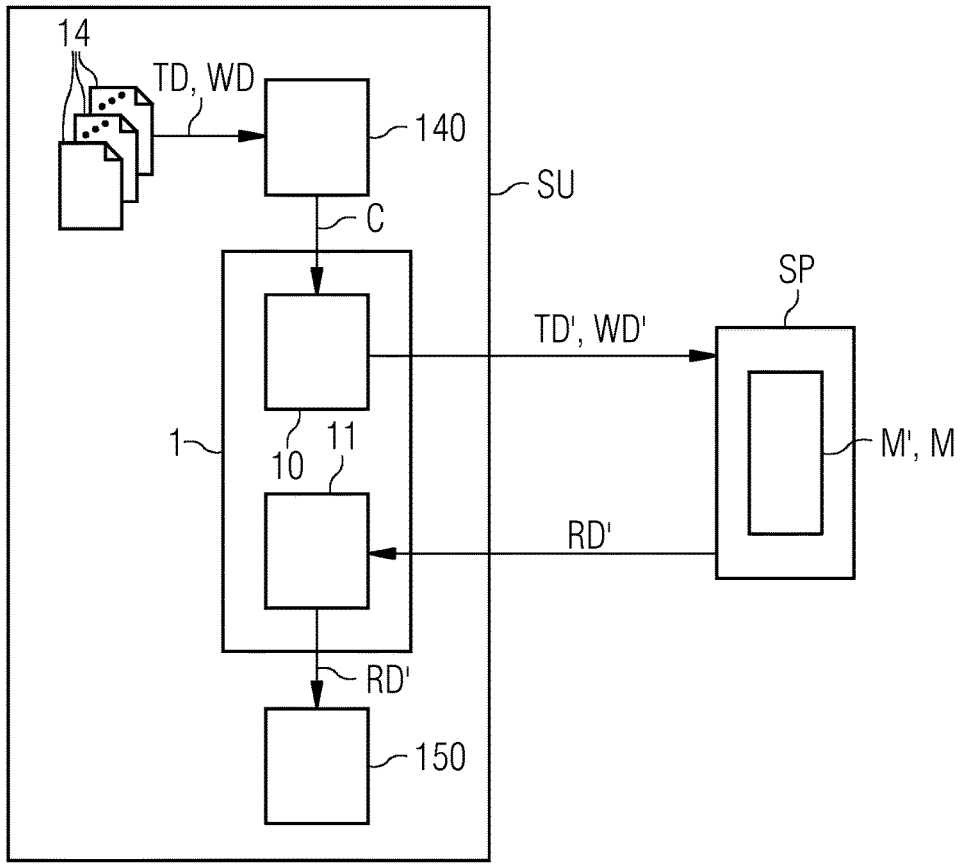
Figure 10:
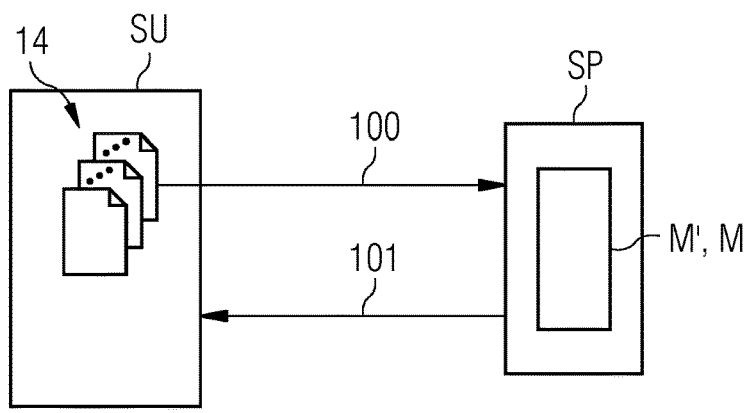

FIGS. 4 and 5 indicate steps of the inventive method applied to process tabular data;

FIG. 6 illustrates a conventional approach to remote processing of tabular data;

FIG. 7 indicates steps of an embodiment of the inventive method applied to process image data;

FIG. 8 illustrates a conventional approach to remote processing of image data;

FIG. 9 indicates steps of an embodiment of the inventive method applied to perform data mining;

FIG. 10 illustrates a conventional approach to remote data mining.

In the diagrams, like numbers refer to like objects throughout. Objects in the diagrams are not necessarily drawn to scale.

According to at least one embodiment of the invention, the method of protecting data exchanged between a service user and a service provider comprises:

encoding upload data by converting relevant content of the upload data into meaningless content;

uploading the encoded upload data to the service provider;

processing the encoded upload data at the service provider to obtain encoded output data;

downloading the encoded output data to the service user; and decoding the encoded output data by converting meaningless content back into relevant content.

In the context of the invention, the expression "encoding upload data" is to be understood as a step of converting the content of the original data into another form such that the underlying nature of the data is retained, but the meaning of the content in the encoded data is no longer evident. The inventive method may therefore also be regarded as a method of anonymizing data exchanged between a service user and a service provider. The step of encoding the upload data should not be understood as a type of encryption. Instead, the encoding step is performed such that the encoded upload data can be processed at the service provider by the same service that was designed to process non-encoded data. From the point of view of the service provider, therefore, it makes no difference whether the service is fed with original data or encoded data, since the encoded data is the "same kind" as the original data. The service will process the encoded data in the same manner, and will provide the "same kind" of results.

An advantage of the method according to an embodiment of the invention is that the data uploaded to the service provider no longer has any "relevant" content, i.e. meaningful content that could be interpreted or understood by an eavesdropper listening in on the connection between service user and service provider, or by any other unauthorized person gaining access to the data at the service provider end. Equally, the download data sent by the service provider to the service user also only contains meaningless content, and the meaningful or relevant content is only revealed when the download data has been decoded again at the service user end. The service user no longer has to rely on expensive and time-consuming encryption to protect the data in transit, and no longer has to depend on the service provider's ability to prevent unauthorized access to the content.

In the method according to an embodiment of the invention, only the service user knows exactly what is behind the data uploaded to the service provider. The service provider or any intruder will not be able to interpret the meaning behind the encoded data. Furthermore, only the service user is able to use an analytical tool that has been trained on the encoded upload data, since these tools will not work with non-encoded data.

According to an embodiment of the invention, the data protection system of a service user comprises an encoder module realized to convert relevant content of upload data into meaningless content prior to uploading from the service user to a service provider;

a data transfer interface realized to upload encoded data to the service provider and to download encoded data from the service provider; and a decoder module realized to convert meaningless content of the download data into relevant content.

An advantage of the data protection system according to an embodiment of the invention is that only an additional encoder module and decoder module are needed to ensure that the sensitive data is never visible to an eavesdropper listening in on the connection between service user and service provider, or to any other unauthorized person gaining access to the data at the service provider end. The encoder module and decoder module can be realized with relatively little effort and can easily be incorporated into an existing setup of the service user. The invention further comprises a computer program product comprising a computer program that is directly loadable into a memory of a control unit of such a data protection system and which comprises program elements for performing relevant steps of the inventive method when the computer program is executed by the control unit of the data protection system.

An embodiment of the invention further comprises a computer-readable medium on which are stored program elements that can be read and executed by a computer unit in order to perform relevant steps of the inventive method according when the program elements are executed by the computer unit.

Particularly advantageous embodiments and features of the invention are given by the claims, as revealed in the following description. Features of different claim categories may be combined as appropriate to give further embodiments not described herein.

The problems relating to data security arise primarily when the service user is remote from the service provider. Data may be transferred or exchanged between service user and service provider over any kind of telecommunications channel, for example over a wireless connection. Equally, data may be stored on data storage devices which are physically transferred between service user and service provider. In the following, it may be assumed that the data link connecting the service user with the remote service provider is a telecommunications channel.

The upload data can comprise training data to be used in training a model. For example, it may be necessary to train a document classifier of a data mining service; to train a neural network of an image segmentation service or image analysis service; to train a prediction model of a data analytics service, etc. Training data is generally annotated manually to assist the model in learning how to correctly classify or process the content. Since the training data is to all intents and purposes no different from "real-life data", and is often directly derived from real-life data, it is important that such training data is also protected from misappropriation.

Once the model at the service provider end has been trained, the service user can request the service provider to perform a service by applying that model to working data. At this stage, the upload data comprises working data to be processed by the trained model. The working data can comprise large quantities of highly sensitive data such as clinical data that is directly related to specific people, and it is important that the working data is protected at all times from misappropriation. To this end, the encoder module is realized to encode tabular documents in preparation for a data processing service provided by the service provider; and/or to encode images in preparation for an image processing service provided by the service provider; and/or to encode text documents in preparation for a document classifier service provided by the service provider.

A key aspect of an embodiment of the invention is that the encoding or transformation does not affect the outcome of the service provided by the service provider, since the encoded data has the same underlying nature as the original data that would be fed to the service. In other words, an analytics tool such as a prediction model using linear regression, logistic regression, classification trees, clustering methods or other statistical data modelling and prediction algorithms will still provide the same results when it is fed with encoded data, as it would when fed with the non-encoded original data. Similarly, a deep-learning image analysis tool that uses an artificial neural network (NN), when fed with encoded images, will provide the same results as the results that it would provide if it was fed with the original non-encoded images.

Download data sent from the service provider to the service user can be model training results, or the results of performing the requested service. The content of the encoded download data is meaningless to anyone that is unaware of the encoding algorithm, so that an eavesdropper or other unauthorized person will be unable to use the download data. At the service user end, the decoder module can decode the received encoded download data to convert the results into a readable version. To this end, the meaningless content in the encoded download data is converted to relevant content once again by applying the inverse operator of the corresponding encoding step. For example, if a look-up table was used to replace specific words in a text document by specific (but meaningless) words of another language, the same look-up table can be used to carry out the reverse operation. Similarly, if the range of a numerical cell entry of an upload spreadsheet was changed linearly by performing division by 100, the actual entry can be retrieved by performing multiplication by 100.

In a particularly preferred embodiment of the invention, the step of encoding the upload data is performed exclusively at the service user end. Equally, the step of decoding the encoded output data is performed exclusively at the service user end. In this way, only encoded data—i.e. meaningless data—is ever sent to the service provider, and the service provider never has access to the original content. An eavesdropper may still "listen in" on the data transfer, but will not be able to interpret the content, so that the stolen information is effectively of no use and of no value. Similarly, a person gaining unauthorized access to the encoded data at the service provider end will not be able to interpret the content, which is effectively of no use and of no value.

Various kinds of data can be processed on a large scale, for example to make predictions, to classify images or documents, etc. In the data protection system according to the invention, the input data is preferably encoded in a specific manner depending on the nature of the data content. In a preferred embodiment of the invention, the input data comprises a number of tabular documents such as worksheets or spreadsheets, and the step of encoding a tabular document comprises replacing a variable name by a neutral identifier and/or rescaling the range of a numerical variable and/or replacing a categorical variable by a number. In this way, any cell entry of a spreadsheet or table is altered beyond recognition, so that content of the encoded document is meaningless and cannot be interpreted within its original context. The operators used to alter the cell entries are preferably noted, and the inverse operators are provided for use during the decoding step. The invention is based on the insight that most known analytics modelling and prediction algorithms such as those used in data mining and machine learning (for example linear or logistic regression, classification and prediction trees, data clustering, etc.) are insensitive to actual data range as long as a linear relationship still remains between the original data range and an "encoded" data range. This invention uses this insight and rescales a numerical variable into another data range such that the initial significance of the variable is no longer evident to any person without knowledge of the encoding operator.

In a further preferred embodiment of the invention, the input data comprises a number of images, and the step of encoding an image comprises one or more of the steps of random pixel remapping and/or pixel scrambling and/or pixel recoloring and/or local image rotation and/or mirroring and/or shifting. Any algorithms used to alter the original image are preferably noted, and the inverse algorithms are preferably provided for use during the decoding step.

To assist in train an image processing model, images of a training data set may be provided with manual annotations. In a preferred embodiment of the invention, the step of encoding an image comprises replacing a manual annotation by a neutral identifier.

In a further preferred embodiment of the invention, the input data comprises a number of text documents, and the step of encoding a document comprises replacing text elements of the document by linguistically unrelated text elements. For example, after pre-processing steps have been carried out on a text document to remove superfluous elements, the remaining words may be replaced by unrelated words in a different language so that it is impossible to identify the nature of the document. In this way, sensitive content related to a person or institution can be effectively rendered meaningless. Alternatively or in addition, the replacement words may be obtained by applying a cipher such as a substitution cipher. If the replacement words are chosen from a different language, this may even be a synthetic language. The words of the original document (s) and their corresponding replacement words may be stored in a look-up table or other record for use during the decoding step.

Figure 1:
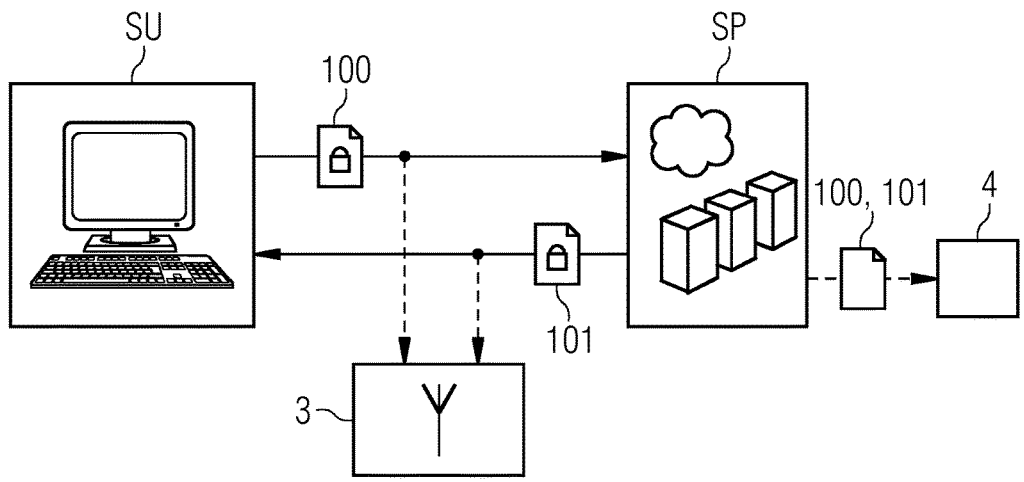
FIG. 1 shows a service user exchanging data with a service provider in a conventional arrangement.

FIG. 1 shows a typical configuration of a service user SU exchanging data 100, 101 with a service provider SP. The service user SU pays for cloud storage and data processing services on hardware provided by the service provider SP. Here, the service user SU sends upload data and service requests to the service provider SP. For example, the service user SU may wish to train a model using training data, or to use a previously trained model to process working data. After completion of the service, the service user SU retrieves the download data 101. In the conventional configuration, it is possible for an eavesdropper 3 to access the data and to use it against the wishes of the service user SU and the service provider SP. It is also possible that a person 4 gains unauthorized access to the upload data 100 and/or the download data 101 at the service provider site, and the unauthorized person 4 may use the data against the wishes of the service user SU and service provider SP.

Figure 2:
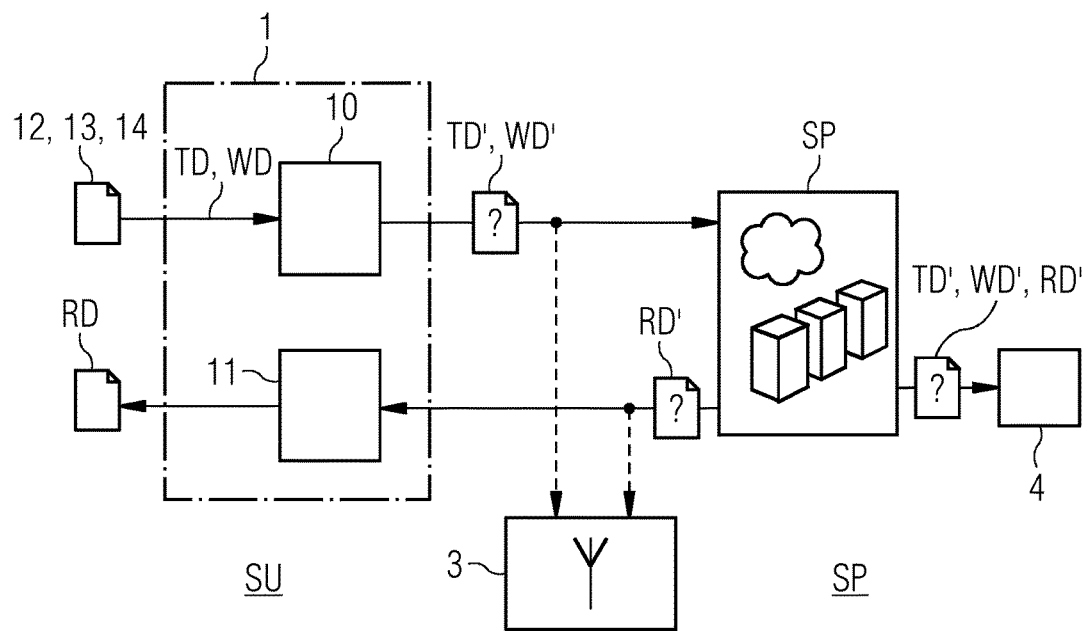
FIG. 2 is a block diagram of an embodiment of the method according to the invention.

FIG. 2 shows a block diagram illustrating the steps of an embodiment of the inventive method. In a first step, upload data is prepared by the service user. The upload data 12, 13, 14 may be training data TD for use in a model training procedure, or working data WD to be processed by a trained model, for example. The data is encoded as described above in an encoder module 10, according to the data type and content. This is followed by a transfer step to transfer the encoded data TD', WD' to the service provider SP. Even if intercepted during transfer, the encoded upload data TD', WD' is meaningless to an eavesdropper 3, as indicated by the question mark. At the service provider SP, data processing is performed on the encoded upload data TD', WD'. The service running at the service provider SP will process the encoded data TD', WD' in the same way as it would process the original data TD, WD, since the form or underlying nature of the original data TD, WD has been preserved during the encoding step. Therefore, the results RD ' are also encoded, but have the same underlying nature as results that would be obtained by processing the original data TD, WD. The encoded results RD' are then returned to the service user SU. Even if intercepted during transfer, or illicitly accessed at the service provider end, the encoded download data RD ' is meaningless to an eavesdropper 3 or unauthorized person 4, as indicated by the question mark. At the service user end, encoded download data RD' undergo a decoding step so that the service user can interpret or read the results RD.

FIG. 3 shows a typical table 12 of patient-related data that might be collected by the service user SU. Information relevant to a particular patient is organized in the table 12, with a first column CI for clinical data fields, a second column C2 for corresponding values for each clinical data field, and a third column C3 for the statistical significance of each value in the second column C2.

In this example embodiment, increasing statistical significance is indicated by increasing numbers of stars. Clinical patient data of this nature—patient age, gender, blood pressure, cholesterol levels—can be used to train a prediction model to estimate the risk of an individual developing cardio-vascular disease (CVD) within the next ten years. However, the information could be used by an eavesdropper to the detriment of the patient and the service user.

FIG. 4 indicates steps of the method described above, and shows the table 12 of FIG. 3 undergoing encoding by an encoder module 10 to give a table of encoded fields. In this case, the encoded table will be used as training data TD' to train a model at the service provider end. All patient-relevant information has been replaced by meaningless data. For example, the "Patient name" field in the first column CI is now an anonymous "Data record ID"; the "HDL cholesterol" field is now an anonymous "Variable 5" etc. Numerical field values in the second column C2 have been scaled in a linear fashion so that for example the patient's age in the left-hand-side table 12 has been encoded into a meaningless number in the right-hand-side table TD'. Text fields have been encoded to numbers, so that the positive "yes" entry relating to diabetes in the left-hand-side table 12 has been replaced by a meaningless "1.0" in the training data TD'. Of course, the encoding described here is only one of many possibilities. Instead of scaling the numerical fields down, these might just as easily be scaled up; instead of replacing words by numbers, they might be replaced by meaningless words instead, so that the word "male" might be replaced by an unrelated word or string of characters. Without knowing the meaning behind the "variables" in the first column of the training data TD', and without knowledge of the encoding algorithm(s) used by the encoder module 10, it is effectively impossible for anyone other than the service user to use or interpret the data.

FIG. 5 illustrates an embodiment of the inventive method. In a training stage, tables of data such as the table 12 shown in the upper part of the diagram are annotated manually by the service user, for example, to indicate whether or not the patients listed in the first column have been diagnosed with cardio-vascular disease. Manual annotations are entered in an additional column C4. Patient-related data values in the various columns of the table 12, along with the annotation values in the final column C4 will be used to train a modelling and prediction algorithm provided by the remote service provider SP. The data shown in the tables is highly sensitive, particularly a clear link between patient name and CVD risk, and must be prevented from falling into the wrong hands when the processing is performed at a remote service provider.

In this example embodiment, the table 12 is encoded using an embodiment of the inventive method as explained above, so that the meaningful content C in the fields of the table 12 are replaced by anonymous and meaningless data X in an encoded table 12'. Entries in a column C4 of annotated values, indicating whether or not the patients listed in the first column of table 12 have been diagnosed with cardio-vascular disease, have also been encoded into a column C4' of meaningless values. Such encoded upload data TD' is then uploaded to the service provider, and is fed to the untrained modelling and prediction algorithm M', which is trained in the usual manner using this data.

Once trained, the service user SU can request the service provider SP to feed the trained modelling and prediction algorithm M with encoded working data WD' as indicated in the lower part of the diagram. The modelling and prediction algorithm M will then return an encoded risk prediction value RD' for each patient, in this case a list of anonymous or meaningless values between 0 and 1. The service user SU can feed the encoded download data RD' into its decoder module 11 to obtain the results RD. In this example, the decoder knows that an encoded download value must be multiplied by 100 to obtain the percent probability quantifying a patient's risk of contracting CVD. In the present example, the service user will see that patient "L. Wald" has a 76% chance of contracting CVD within the next 10 years.

As explained above, the conventional approaches either fail to prevent data theft by eavesdropping or by unauthorized access at the service provider end. FIG. 6 shows such a conventional arrangement of a modelling and prediction algorithm PM provided by a service provider SP to a service user. Here, the training data 100, working data 100 and the results 101 returned by the model are sent over a data link between service user SU and service provider SP, and are therefore vulnerable to eavesdropping over the data link, and are also vulnerable to illicit use at the service provider end. The inventive method is applicable also to image data.

FIG. 7 shows encoding and decoding stages applied when the service user SU requests processing or analysis of images 13 by a deep neural network M provided by the service provider SP. Before uploading image data over a connection between service user SU and service provider SP, the image data 13 is encoded to render it meaningless to anyone not in possession of the encoding algorithm. If the image 13 is to be used to train a deep neural network M', manual annotations 130 may be added for training purposes, and these annotations 130 are also encoded. The encoded data TD', WD' is then sent to the service provider SP, where it is used to train a deep neural network M' to perform a specific task (e.g. radiographic image segmentation, landmark detection etc.), or interpreted by the trained neural network M.

The diagram shows an artificial neural network (ANN) M realized to connect to all pixels in an image with iterative training algorithms and realized to adjust the weights of every inter-neural connection such that the output layer optimally classifies the input image or detects particular landmarks in the image. An embodiment of the invention is based on the insight that an additional input layer can be added by the encoder module 10, performing an image transformation that does not in any way affect the ability of the neural network to be trained and optimized to recognize image features. The trained deep neural network M returns encoded results RD' over the data link, and the service user SU can apply the decoder module 11 to obtain the results RD.

FIG. 8 shows a conventional configuration with a deep neural network M provided by a service provider SP. A service user SU wishing to avail of the deep neural network M must upload image data 100 over a data link. Any eavesdropper can access the image data 100 and/or any image processing results 101 on their way from the service provider SP to the service user SU. Equally, the images 100 and analysis results 101 might be vulnerable to authorized access at the service provider SP. The inventive method is applicable also to data or text mining.

FIG. 9 shows encoding and decoding stages of the inventive method when applied to a set of documents 14 to be processed by a document classifier algorithm M provided by a remote service provider SP. Each document 14 is initially processed by a pre-processor 140, for example to remove all formatting, to convert all text to lower case, to remove punctuation, etc. The result of pre-processing is a set of documents containing only plain text.

Applying an embodiment of the inventive method, the encoder module 10 converts the meaningful content C remaining in each document by meaningless content. Encoding can be performed by using a straightforward cipher, by replacing each word by a different, unrelated word according to a look-up table, etc.

Replacement words can be in a foreign or synthetic language. During a training stage, manual class encoding is performed on the documents 14 that will be used to train an as yet untrained document classifier M'. For example, the classes "Tax Return" and "Medical Record" may be encoded to the anonymous "Class 0" and "Class 1", respectively, and the training data TD' relates each encoded document with its appropriately encoded class. The encoded training documents TD' are sent along with their encoded document classes to the remote service provider SP, which then initiates the training procedure on the received data TD'.

Later, the service user SU can carry out the preprocessing steps on any number of as yet unclassified documents 14, upload the encoded working data WD' to the service provider SP, and request that the trained document classifier M processes the working data WD'. The service provider SP then returns an encoded result RD'—i.e. an encoded class—for each of the documents in the working data WD'. The service user SU can then apply the decoder module 11 to decode the download results RD' to obtain the document classes RD. A subsequent unit or module 150 can then assign each document to the document class determined by the document classifier M.

FIG. 10 shows a conventional configuration with a document classifier M provided by a service provider. A service user SU wishing to avail of the document classifier service must upload sensitive document data 100 over a data link between service user and service provider. Any eavesdropper can access the document data 100 and the classifier results 101 over the data link between service provider and service user. Equally, the data 100, 101 might be vulnerable to authorized access at the service provider SP.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method of protecting data exchanged between a service user and a service provider, the method comprising:
encoding input data by converting meaningful content of the input data into meaningless content to obtain encoded upload data for sending to the service provider, the input data including a number of tabular documents, wherein the encoding of the input data, including the number of tabular documents, includes resealing of a range of a numerical variable such that a linear relationship remains between an original data range of the input data and an encoded data range of the input data;
processing the encoded upload data at the service provider by using analytics modeling, statistical data modeling or prediction algorithms, to obtain encoded download data for sending to the service user; and
decoding the encoded download data by converting meaningless content of the encoded download data into meaningful content of download data.

2. The method claim 1, wherein the encoding of the input data is performed such that the encoded upload data is processable at the service provider by a service designed to process non-encoded data.

3. The method of claim 1, wherein at least one of
the encoding of the input data to obtain the encoded upload data is performed by the service user, and
the decoding of the encoded download data is performed by the service user.

4. The method of claim 1, wherein the encoding of the input data including the number of tabular document includes at least one of replacing a variable name by a neutral identifier and replacing a categorical variable by a number.

5. The method of claim 1, wherein the service user further requests processing or analysis of images by a deep neural network provided by the service provider, wherein the input data includes the images and wherein the encoding of the input data includes encoding of the images, further including adding an additional input layer, performing an image transformation that does not affect an ability of the neural network to be trained and optimized to recognize image features of the images.

6. The method of claim 5, wherein an image, of the images, is provided with a number of manual annotations, and wherein the encoding of the input data includes encoding of the image, including replacing a manual annotation, of the number of manual annotations, by a neutral identifier.

7. The method of claim 1, wherein the input data further includes a number of text documents, and wherein the encoding of the input data, including encoding a document of the number of text documents, includes replacing text elements of the document by unrelated text elements.

8. The method of claim 7, wherein the unrelated text elements are at least one of
fetched from a look-up table,
obtained from a different language, and
obtained by applying a substitution cipher to the text elements.

9. The method of claim 1, wherein the encoded upload data includes encoded training data to be used in training a model used in a service provided by the service provider, and wherein the download data includes results from the training of the model used in the service.

10. The method of claim 1, wherein the encoded upload data includes encoded working data, to be processed by a trained model used in a service provided by the service provider, and wherein the download data includes results from the service.

11. The method of claim 1, wherein meaningless content of the encoded download data is converted to relevant content by applying an inverse operator of corresponding encoding.

12. A data protection system, comprising:
an encoder module adapted to encode input data by converting meaningful content of the input data into meaningless content to obtain encoded upload data for sending to a remote service provider, the input data including a number of tabular documents, wherein the encoder module is adapted to encode the input data including the number of tabular documents, including being adapted to rescale a range of a numerical variable, the encoder module being adapted to rescale the range of the numerical variable such that a linear relationship remains between an original data range of the input data and an encoded data range of the input data;
a service provider adapted to process the encoded upload data by using analytics modeling, statistical data modeling or prediction algorithms, to obtain encoded download data for sending to a service user; and
a data transfer interface adapted to upload the encoded upload data to the service provider and to receive encoded download data from the service provider; and
a decoder module adapted to convert the encoded download data into download data including meaningful content.

13. The data protection system of claim 12, wherein the encoder module is adapted to at least one of
encode tabular documents in preparation for a data processing service provided by the service provider;
encode images in preparation for an image processing service provided by the service provider; and
encode text documents in preparation for a document classifier service provided by the service provider.

14. A non-transitory computer program product storing a computer program, directly loadable into a memory of a control unit of a data protection system, including program elements for performing the method of claim 1 when the computer program is executed by the control unit of the data protection system.

15. A non-transitory computer-readable medium, storing stored program elements, readable and executable by a computer unit, to perform the method of claim 1 when the program elements are executed by the computer unit.

16. The method of claim 2, wherein at least one of
the encoding of the upload data is performed by the service user, and
the decoding the encoded download data is performed by the service user.

17. The method of claim 2, wherein the encoding of the input data including the number of tabular document includes at least one of replacing a variable name by a neutral identifier and replacing a categorical variable by a number.

18. The method of claim 2, wherein the service user further requests processing or analysis of images by a deep neural network provided by the service provider, wherein the input data includes the images and wherein the encoding of the input data includes encoding of the images, further including adding an additional input layer, performing an image transformation that does not affect an ability of the neural network to be trained and optimized to recognize image features of the images.

19. A data protection system, comprising:
a first memory storing computer-readable instructions; and
one or more processors configured to execute computer-readable instructions to
encode input data, by converting meaningful content of the input data into meaningless content to obtain encoded upload data for sending to a remote service provider, the input data including a number of tabular documents, wherein encoding of the input data, including the number of tabular documents, includes rescaling of a range of a numerical variable, the rescaling being such that a linear relationship remains between an original data range of the input data and an encoded data range of the input data,
process the encoded upload data by using analytics modeling, statistical data modeling or prediction algorithms, to obtain encoded download data for sending to a service user,
upload the encoded upload data to the service provider and to receive encoded download data from the service provider, and
convert the encoded download data into download data including meaningful content.

* * * * *